United States Patent
Parada

(10) Patent No.: US 7,314,911 B2
(45) Date of Patent: Jan. 1, 2008

(54) PROSTATE HYPERPLASIA THERAPY

(75) Inventor: Luis F. Parada, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 45 days.

(21) Appl. No.: 10/920,886

(22) Filed: Aug. 17, 2004

(65) Prior Publication Data

US 2006/0040854 A1    Feb. 23, 2006

(51) Int. Cl.
*A61K 38/16* (2006.01)

(52) U.S. Cl. ..................................................... 530/303

(58) Field of Classification Search ..................... None
See application file for complete search history.

(56) References Cited

OTHER PUBLICATIONS

Lamb DJ, Zhang L Challenges in prostate cancer research: animal models for nutritional studies of chemoprevention and disease progression. J. Nutr. Dec. 2005;135(12 Suppl):3009S-3015S.*

Carlson GA, Borchelt DR, Dake A, Turner S, Danielson V, Coffin JD, Eckman C, Meiners J, Nilsen SP, Younkin SG, Hsiao KK., Genetic modification of the phenotypes produced by amyloid precursor protein overexpression in transgenic mice, Hum Mol Genet. 1997.*

Lok S., et al, "Identification of INSL6, a new member of the insulin family that is expressed in the testis of the human and rat," Biol Reprod. Jun. 2000;62(6):1593-9.*

* cited by examiner

*Primary Examiner*—Cecilia J. Tsang
*Assistant Examiner*—T. S Heard
(74) *Attorney, Agent, or Firm*—Richard Aron Osman

(57) ABSTRACT

The invention is a method for treating prostate hyperplasia by contacting a patient with insulin-6 in an amount effective to prevent or reduce prostate hyperplasia. The invention includes transgenic insulin-6 knockout mice that exhibit prostate hyperplasia and that can be used in screening agents for anti-prostate hyperplasia activity.

5 Claims, No Drawings

PROSTATE HYPERPLASIA THERAPY

FIELD OF THE INVENTION

The field of the invention is modulating insulin-6 signaling to control prostate growth.

BACKGROUND OF THE INVENTION

Abnormal prostate growth is most commonly associated with Benign Prostate Hyperplasia (BPH) or prostate cancer. By age 50, one-third of American men have microscopic signs of prostate cancer, and by age 75, one-half to three-quarters of men's prostates will have cancerous changes. Most of these cancers either remain latent, producing no signs or symptoms, or they are so slow-growing, or indolent, that they never become a serious threat to health. A much smaller number of men will actually be treated for prostate cancer. About 16 percent of American men will be diagnosed with prostate cancer during their lifetime; 8 percent will develop significant symptoms; and 3 percent will die of the disease. The causes of prostate cancer are not well understood.

Risk factors include: 1) Age. In the United States, prostate cancer is found mainly in men over age 55. The average age of patients at the time of diagnosis is 70. 2) Family history of prostate cancer. A man's risk for developing prostate cancer is higher if his father or brother has had the disease. 3) Race. This disease is much more common in African American men than in white men. It is less common in Asian and American Indian men. 4) Diet and dietary factors. Some evidence suggests that a diet high in animal fat may increase the risk of prostate cancer and a diet high in fruits and vegetables may decrease the risk.

Studies are in progress to learn whether men can reduce their risk of prostate cancer by taking certain dietary supplements. Although a few studies suggested that having a vasectomy might increase a man's risk for prostate cancer, most studies do not support this finding. Scientists have studied whether benign prostatic hyperplasia, obesity, lack of exercise, smoking, radiation exposure, or a sexually transmitted virus might increase the risk for prostate cancer. At this time, there is little evidence that these factors contribute to an increased risk.

BPH is the abnormal growth of benign prostate cells. In BPH, the prostate grows larger and presses against the urethra and bladder, interfering with the normal flow of urine. More than 50 percent of the men in the United States between the ages of 60 and 70 and as many as 90 percent between the ages of 70 and 90 have symptoms of BPH. About 50 percent of men with BPH develop symptoms serious enough to warrant treatment.

The prostate normally starts out about the size of a walnut. By the time a man is age 40, the prostate may already have grown to the size of an apricot; by the age of 60, it may be as big as a lemon. BPH is a troublemaker because the prostate, as it enlarges, presses against the bladder and the urethra, blocking the flow of urine. A man with BPH may find it difficult to initiate a urine stream or to maintain more than a dribble. He also may need to urinate frequently, or he may have a sudden, powerful urge to urinate. Many men are forced to get up several times a night; others have an annoying feeling that the bladder is never completely empty. Straining to empty the bladder can make matters worse; the bladder stretches, the bladder wall thickens and loses its elasticity, and the bladder muscles become less efficient. The pool of urine that collects in the bladder can foster urinary tract infections, and trying to force a urine stream can produce backpressure that eventually damages the kidneys.

The kidneys are where urine is formed, as waste products are filtered from the blood. BPH sometimes leads to problems. For instance, a completely blocked urethra is a medical emergency requiring immediate catheterization, a procedure in which a tube called a catheter is inserted through the penis into the bladder to allow urine to escape. Other serious potential complications of BPH include bladder stones and bleeding. BPH cannot be cured, but its symptoms can be relieved by surgery or by drugs in many cases.

Although the popularity of prostate surgery has diminished since drug therapy became available (a total of 250,000 procedures were performed in 1996, down from 400,000 in 1988), operations for BPH remain the most common surgery performed on American men. Several types of surgery can relieve the symptoms of an enlarged prostate. They are: transurethral resection of the prostate (TURP), transurethral incision of the prostate (TUIP), transurethral needle ablation (TUNA), and open prostatectomy.

TURP accounts for more than 90 percent of all BPH surgeries. The procedure relieves symptoms quickly, typically doubling the urinary flow within weeks. Using either a tiny blade or an electric loop, the surgeon pares away the urethra's lining and bits of excess prostate tissue. Gradually the passageway is expanded. A TURP patient is usually hospitalized for several days after surgery. During convalescence, a catheter remains in the bladder through the penis to drain out urine. About 5 percent of men become partially incontinent after the TURP procedure-although the incontinence sometimes clears up over time. In addition, some men develop scarring in the urethra that can block urination. As many as 10 percent will need repeat surgery because prostate tissue grows back. About 5 percent of men become impotent after the TURP procedure. But TURP does not usually affect a man's ability to have an erection or an orgasm, since the nerves that control erection lie outside the prostate and are not touched by the operation. A more common side effect is a dry, or retrograde, ejaculation. It occurs after surgery when the neck of the bladder fails to close properly during ejaculation. The result is that semen spurts backward into the bladder rather than through the penis. Men who experience this side effect still have the sensation of an orgasm but are unable to father children.

Transurethral incision of the prostate (TUIP) is used on small prostate glands of 30 grams or less and is used far less frequently than TURP. Like TURP, TUIP is performed by passing an instrument through the penis to reach the prostate. The difference is that a doctor makes only one or two small cuts to relieve pressure in the prostate rather than trimming away tissue. Like TURP, the procedure considerably increases the urine flow.

Transurethral needle ablation (TUNA) uses radio frequency energy delivered through needles to kill excess prostate tissue. A catheter that deploys the needles toward the obstructing prostate tissue is inserted into the urethra before the procedure begins. Some clinical studies have reported that TUNA improves the urine flow with minimal side effects when compared with other procedures.

Open prostatectomy is another surgical method for treatment of enlarged prostate. The word "open" refers to the fact that a surgeon makes an incision to reach the prostate, instead of inserting an instrument through the urethra. Open prostatectomy may involve either a radical or a partial procedure. A radical prostatectomy, which removes the whole prostate, is done for cancer. The incision is made through either the lower abdomen or the perineum. Partial prostatectomy, which leaves the posterior portion of the prostate intact, is used to treat BPH. The incision for a partial prostatectomy is usually through the abdomen. Open prostatectomy once was the sole recourse for an enlarged prostate. Today it is used only on extremely large prostates, which represent about 5 percent of all cases.

As an alternative to surgery, drug therapy has been effective in the treatment of BPH. Two major classes of drugs are used: alpha adrenergic blockers and finasteride. Alpha adrenergic blockers were originally used for the treatment of high blood pressure, to relax smooth muscles in blood vessel walls. In BPH, they relax the muscular portion of the prostate and the bladder neck. This allows urine to flow more freely. In the average patient, these drugs increase the rate of urine flow and reduce symptoms, often within days. Side effects include dizziness, fatigue, and headache.

Finasteride shrinks the prostate by blocking an enzyme that converts the male hormone testosterone into a more potent, growth-stimulating form. Some, but not all, studies show that taking finasteride for at least six months can increase urinary flow rate and reduce symptoms. It seems to work best for men who have greatly enlarged prostates. In a small percentage of men, the drug can affect sexual activity, decreasing a man's interest in sex, diminishing his ability to have an erection, and causing problems with ejaculation. It sometimes also causes tenderness or swelling of the breasts. It may cause a drop in PSA levels.

In summary, prostate cancer and BPH are common ailments of aging men with the cost to health care reaching the billions of dollars. The present treatments, though effective in some cases (hormonal/surgical), are mostly palliative in nature and can have considerable side effects (incontinence, impotence, recurrence, high cost). The underlying molecular basis for prostate hypertrophy remains unclear and therefore, the development of tailored therapies that treat the underlying cause cannot be devised.

The Insulin-related gene family is comprised of structurally related proteins with diverged functions. These peptide hormones are known to regulate cell growth, metabolism and several tissue-specific functions. Members of this family include insulin, insulin like growth factors 1 and 2 (IGF I, 11), relaxin, Insulin 3, Insulin 4, Insulin 5, and Insulin 6. The length of the C-peptide as well as presence of additional D and E peptides at the end distinguish proIGFI and II from the rest of the insulin-related family members. These peptide hormones are synthesized as preprohormones comprising of a signal peptide, a B-chain, a connecting C-peptide, and an A-chain. The mature proteins are generated by proteolytic cleavage of the signal and the connecting peptide by prohormone convertases, and the joining of the A- and the B-chains by inter- and intra-disulfide bonds. The spacing of the cysteine residues is conserved, and it is the conserved cysteine motif, the signal peptide, conserved glycine at the end of the B-peptide, and a few conserved hydrophobic residues in the A- and B-peptide that provide a signature for classification of proteins into insulin gene family.

Insulin 6 (Ins16) was identified through the insulin gene family signature motif from the expressed sequence tag (EST) databases by several groups in numerous and varied mammalian species, including mice, rats, and humans (see, e.g. Lok et al., Biol Reprod. 2000 Jun;62(6):1593-9). The deduced coding region of mouse Ins16 is 191 amino acids and the human Ins 16 is 213 amino acids. The difference in the prohormone length between the mouse and the human is due primarily to the slightly longer C-peptide in the humans. The predicted B-domain is 34 amino acids and the A-domain is 38 amino acids, thus making the mature Ins16 peptide 72 amino acids long. The putative B- and A-domains of human are ~55% identical to mouse Ins16, 43% to human relaxin, 38% to Insulin 3, 36% to human Insulin, 36% to IGFII, 33% to IGFI, 28% to Insulin 5, and 24% to Insulin 4.

Relevant Literature

Relevant literature includes Lok et al., Biol. Reprod. 62 (6), 1593-1599 (2000); U.S. Pat. No. 5,959,075; and S. Y. Hsu, Mol. Endocrinol. 13 (12), 2163-2174 (1999).

SUMMARY OF THE INVENTION

The inventors disclose that prostate size can be regulated by modulating insulin-6 levels: model animals treated to inhibit insulin-6 levels are shown to exhibit prostate hyperplasia, and conversely, animals treated to increase insulin-6 levels exhibit atypically small prostates. The invention provides the use of insulin-6 and insulin-6 expression vectors to reduce prostate hyperplasia, insulin-6 knockout mice and their use as a model for prostate hyperplasia, and pharmaceutical compositions comprising insulin-6. Included are related pharmaceutical compositions, therapeutic methods, gene therapy, transgenic mice, screening methods, etc.

One aspect of the invention is a method for treating prostate hyperplasia, the method comprising the step of contacting a human patient determined to be subject to or predisposed to prostate hyperplasia with an effective amount of insulin-6. In one embodiment, the prostate hyperplasia is benign prostate hyperplasia (BPH). In another embodiment, the prostate hyperplasia is prostate cancer. The insulin-6 can be produced recombinantly, synthetically, or by biochemical isolation. In a further embodiment, prior to administering the insulin-6, it is determined that the patient is subject to or predisposed to the prostate hyperplasia. The insulin-6 can be administered directly to the patient, or in another embodiment, is expressed by a transcript introduced into the patient. The method may further comprise, after the administering step, the step of detecting in the patient a reduction in growth or size the prostate hyperplasia.

Another aspect of the invention is a method of determining whether a patient may benefit from insulin-6 therapy, the method comprising the steps of obtaining a biological sample from the patient and testing the sample for abnormal insulin-6 expression relative to a control, wherein detection of abnormal insulin-6 expression is indicative that a patient may benefit from insulin-6 therapy. In one embodiment, the patient is predetermined to have prostate hyperplasia. The method may test for the underexpression of insulin-6, or in another embodiment, the expression of mutant insulin-6.

Another aspect of the invention is a transgenic insulin-6 knockout mouse, wherein the mouse is determined to be subject to or predisposed to prostate hyperplasia as a result of the insulin-6 knockout.

A further aspect of the invention is a method for screening an agent for anti-prostate hyperplasia activity, the method comprising the step of treating an insulin-6 knockout mouse with a candidate agent, and determining if the treatment effects a reduction in growth or size of prostate hyperplasia in the mouse.

DETAILED DESCRIPTION OF PARTICULAR EMBODIMENTS OF THE INVENTION

One aspect of the invention is a method for treating prostate hyperplasia, the method comprising the step of contacting a human patient determined to be subject to or predisposed to prostate hyperplasia with an effective amount of insulin-6. In one embodiment, the prostate hyperplasia is benign prostate hyperplasia (BPH). In another embodiment, the prostate hyperplasia is prostate cancer.

The insulin-6 for the subject methods may be obtained from a variety of sources. For example, insulin-6 may be exogenously produced recombinantly, synthetically, or by biochemical isolation. Recombinant methods for producing insulin-6 are known in the art (see e.g. U.S. Pat. No. 5,959,075). Synthetic methods for producing insulin-6 include direct peptide synthesis using solid-phase techniques (e.g. Solid-Phase Peptide Synthesis, Methods in Enzymology, Ed. Fields, G. B., 1997, Academic Press, San Diego; Lebl M., Leblova Z., 2004, Dynamic database of references in solid phase synthesis. Internet: http://www.5z.com). For biochemical isolation, the insulin-6 can be obtained from tissues and cells that express the protein. Insulin-6 is naturally expressed in the genitourinary organs after birth, particularly in the postpubertal testis. Our tissue expression analyses indicate high levels of insulin-6 expression within the testis (in the seminiferous tubules in spermatocytes and round spermatids), and within the adult female reproductive system (in cells of the oviduct and the uterus). Our data also indicate insulin-6 expression in the skin, spleen, skeletal muscle, placenta, liver, lung, spinal cord, adrenal gland, lymph nodes, trachea, bone marrow, and brain (in the olfactory and vomeronasal epithelium).

The protein may be purified from other cellular and non-cellular components, preferably to at least 80% purity (protein weight); preferably, to purity of at least 90%, 95%, or 99% pure. Protein purity may be assessed by any means known in the art, such as SDS-polyacrylamide gel electrophoresis.

Pharmaceutical preparations of insulin-6 protein may be prepared for storage and subsequent administration by mixing the protein having the desired degree of purity with pharmaceutically acceptable carriers, excipients, or stabilizers (Remington and Gennaro; Remington: The Science and Practice of Pharmacy, 1990, Mack Publishing Co., 18th edition, ISBN: 0912734043). Such therapeutic formulations can be in a variety of forms, including lyophilized formulations or aqueous solutions, and may be accompanied with labeling or product inserts with instruction on how to administer the preparation for treatment or prophylaxis of prostate hyperplasia.

In a further embodiment, prior to administering the insulin-6, it is determined that the patient is subject to or predisposed to the prostate hyperplasia. This can be accomplished using known methods. For example, elevated levels of prostate specific antigen (PSA) are indicative of prostate cancer or BPH (Naz et al., J Coll Physicians Surg Pak. 2004 February;14(2):69-71). Other known methods include assessing for enlarged prostate, and prostate biopsy to detect hyperplastic cells. Predisposition to prostate hyperplasia may be determined by diagnosing a defect in the insulin-6 signaling pathway, as discussed further below, or other biological pathways known to be involved in prostate growth and development. Other medical assessment, such as identification of risk factors and/or family history of prostate hyperplasia may also be used to assess predisposition to prostate hyperplasia.

The insulin-6 can be administered directly to the patient, or in another embodiment, expressed by a transcript introduced into the patient. For direct administration to the patient, known methods for administration of protein therapeutics can be used. Modes of delivery may by regionally restricted or systemic, and include intravenous administration as a bolus or by continuous infusion over a period of time, by intramuscular, intratesticular, intraprostatic, intraperitoneal, intracerebrospinal, subcutaneous, intra-articular, intrasynovial, intrathecal, oral, topical, or inhalation (intranasal, intrapulmonary) routes. Effective and optimized dosages and routes of administration are informed from vast clinical experience with related insulin protein delivery, and can be further determined empirically, and from cell and animal models. Typically, a daily dosage will vary from about 10 ng protein/kg body weight up to about 100 mg protein/kg body weight, depending upon the route of administration.

For indirect delivery of the insulin-6, the protein is typically expressed by a transcript introduced into the patient. In one example, transgenic cells that express an insulin-6 encoding transgene are transplanted into a patient's testicles using methods such as described by Dufour et al. (Gene Ther. 2004 April;11(8):694-700). In an alternative embodiment, a patient's endogenous insulin-6 gene is upregulated using artificial transcription factors (Yaghmai R, Cutting G R, Mol Ther. 2002 June;5(6):685-94).

The methods may further comprise, after the administering step, the step of detecting in the patient a reduction in growth or size the prostate hyperplasia. Methods for detecting changes in prostate growth or size are referenced herein and are known in the art. In addition, the methods may further comprise prior to the administering step, the step of determining that the patient abnormally underexpresses insulin-6. Accordingly, the invention provides methods of determining whether a human patient determined to be subject to or predisposed to prostate hyperplasia patient underexpresses insulin-6 by obtaining a biological sample from the patient and testing the sample for abnormal, insulin-6 underexpression relative to a control.

In a related aspect, the invention provides a method of identifying patients determined to have abnormal, insulin-6 underexpression, and therefore provide preferred patients for the disclosed insulin-6 therapy. For example, this embodiment may comprise the steps of obtaining a biological sample from a candidate patient and testing the sample for abnormal insulin-6 underexpression relative to a control, wherein detection of abnormal insulin-6 expression indicates that the patient is a preferred subject for insulin-6 therapy. The biological sample may be taken from a tissue or cell-type that otherwise normally expresses insulin-6, such as the seminiferous tubules in spermatocytes and round spermatids. In a more particular embodiment, the patient is predetermined to have or be predisposed to prostate hyperplasia. Detection of abnormal insulin-6 expression results in the patient being prescribed an insulin-6 treatment regimen, such as disclosed herein.

Reagents and methods well-known in the art can be used to test a patient sample for abnormal insulin-6 expression. For example, reagents such as insulin-6 specific oligonucleotides or antibodies directed against insulin-6 can be used to detect insulin-6 gene mutations, an over- or under-expression of insulin-6 mRNA, an over- or an under-abundance of insulin-6 gene product, perturbations or abnormalities in the insulin-6 signal transduction pathway, etc. Methods that can be used include Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). In one embodiment, the patient is tested for underexpression of insulin-6, i.e. production of abnormally low levels relative to normal control. For example, a Northern blot analysis of mRNA from testicular tissue obtained from the patient, using full or partial insulin-6 cDNA sequences as probes, can determine whether the patient produces low levels of insulin-6, and thus may benefit from insulin-6 therapy. In another embodiment, the patient is tested for expression of mutant or otherwise nonfunctional insulin-6. Insulin-6 function or activity is readily determined in cell and animal-based assays.

Another aspect of the invention is a transgenic insulin-6 knockout mouse, wherein the mouse is determined to be subject to or predisposed to prostate hyperplasia as a result of the insulin-6 knockout. Typically, the knock-out mouse has a heterozygous or homozygous alteration in the sequence of its endogenous insulin-6 gene that results in a decrease of insulin-6 function, preferably such that insulin-6 expression is undetectable or effectively reduced. The knock-out mouse appears normal when born, but as a young adult, displays an abnormal prostate phenotype; specifically, there is disorganization and hyperplasia of the prostate. Thus, the knock-out mouse of the invention is subject to or predisposed to prostate hyperplasia as a result of the insulin-6 knockout, and provides useful model for the disease. Knock-out animals are typically generated by homologous recombination with a vector comprising a transgene having at least a portion of the gene to be knocked out. Typically a deletion, addition or substitution has been introduced into the transgene to functionally disrupt it. Detailed methodologies for homologous recombination in mice are available (see Capecchi, Science (1989) 244:1288-1292; Joyner et al., Nature (1989) 338:153-156).

A further aspect of the invention is a method for screening an agent for anti-prostate hyperplasia activity, the method comprising the step of treating an insulin-6 knockout mouse with a candidate agent, and determining if the treatment effects a reduction in growth or size of prostate hyperplasia in the mouse.

EXAMPLE I

Insulin-6 Expression Analysis

We examined the tissue distribution of insulin-6 (Ins16) in the mouse and found that its expression is confined to genitourinary organs after birth. It is primarily expressed in the postpubertal testis. The primary size of the Ins16 transcript is ~1.2 kb but additional longer transcripts were observed in the postpubertal testis. Expression, by in situ hybridization was first detected in the follicles of vibrissa at embryonic day (E) 13.5. No other sites of expression were observed at E13.5. Low levels of transcripts were detected in both male and female reproductive tissues as early as E17.5 by Northern analysis. Ins16 mRNA in the testis was detectable at post-natal day (P) 7, and reached maximum levels in the adult. Within the testis, Ins16 transcripts were observed in the seminiferous tubules in spermatocytes and round spermatids. Expression was not observed in any other cells in the testis such as Leydig, Sertoli, or peritubular myeloid cells or the epididymis. Low levels of Ins16 transcripts have been observed in the prostate in the rat but not in the human. In the adult female reproductive system, a subset of cells in the oviduct and the uterus express Ins16, however no expression is observed in the ovary. Ins16 transcripts were observed in the skin, spleen, skeletal muscle, placenta, liver, lung, spinal cord, adrenal gland, lymph nodes, trachea and bone marrow. Within the brain, Ins16 mRNA is observed in the olfactory and vomeronasal epithelium. Other sites of expression in the adult brain have not been investigated by in situ hybridization analysis.

The Ins16 gene has been mapped to chromosome 19 in mouse, and to a syntenic region on chromosome 9 in humans. Interestingly, the mouse relaxin gene is located approximately 3 kb upstream of the Ins16 gene, and both human relaxin genes and Ins14 have been mapped to chromosome 19, close to the Ins16 gene. The chromosomal arrangements of the Insulin-gene family members support the contention that these genes have originated by gene duplications several times throughout evolution. The Ins16 gene, similar to some other members of the family, is encoded by two exons that are separated by a single 3.3 kb intron. The first exon contains the initiator methionine, signal peptide, the B-peptide, and ⅓rd of connecting C-peptide, the second exon encodes the rest of the C-peptide and the A-peptide. The members of the insulin-gene family play diverse roles in cell growth, proliferation, metabolism, and reproduction. Ins13, another member of this family, which is synthesized primarily by Leydig cells in testis, plays important role in testicular descent which is critical for of Ins16 expression role in reproduction male, disruption of proper spermatogenesis to take place. The site suggests that Ins16 may also play an important in both males and females. For example, in the Ins16 function may lead to improper formation or maturation of the spermatozoa or their motility, whereas in the female Ins16 may play a role in parturition.

EXAMPLE 2

Insulin-6 Knockout Mice

The Ins16 gene is knocked out in mice through homologous recombination (Zimmermann et al., Mol Endocrinol. 1999 May;13(5):681-91.). A replacement targeting vector is designed to delete the two exons encoding the Ins16 factor and is replaced with the neomycin phosphotransferase (neo) gene under the control of the phosphoglycerate kinase promoter. Introduction of a negative selection marker, the herpes simplex virus thymidine kinase (tk) gene, at the 3'-end of the construct enables the use positive and negative selection (Mansour et al., 1988, Nature 336:348-352). MP1 ES cells are transfected with the targeting vector and selected for homologous recombination events (Voss et al., 1997, Exp Cell Res 230:45-49). Drug-resistant clones are selected, and DNA is isolated and screened by Southern blot analysis using an external probe. Recombinant clones that have undergone homologous recombination and that produce germ line-transmitting chimeras after aggregation with morula derived from CD1 females are selected. These chimeras are bred with CD1 and 129/Sv females to establish the Ins16-deleted allele on a CD1×129/Sv hybrid and a 129/Sv inbred genetic background. Southern blot analysis on DNA isolated from tail biopsies is used to determine the genotype of the offspring.

Using knockout technology, we generated a mouse strain that lacks the Insulin 6 gene. Mice lacking this gene and its protein product are born and appear normal. We dissected several young adult males and found clear evidence of postate disorganization and hyperplasia, indicating that insulin-6 signaling regulates prostatic growth.

EXAMPLE 3

Insulin-6 Overexpression Reduces Prostate Size

Insulin-6 was overexpressed by transgenic expression using an insulin promoter. Since pancreatic beta cells possess the catalytic pathways to appropriately process insulin like molecules, we adapted to insulin-6 a prior study of insulin3 overexpression: Adham et al., Mol Endocrinol. 2002 February;16(2):244-52. Briefly, transgenic male mice were generated that overexpressed Ins16 in the pancreas during fetal and postnatal life. Expression of the transgenic allele resulted reduced prostate size, again indicating that insulin-6 signaling regulates prostatic growth.

EXAMPLE 4

Use of Insulin-6 Knockout Mice in Drug Screening

Transgenic insulin-6 knockout mice that are subject to or predisposed to prostate hyperplasia as a result of the insulin-6 knockout obtained as described above are used to screen a peptide and synthetic pharmacophore-based library for anti-prostate hyperplasia activity using methodology adapted from Guo et al. (Biol. Pharm. Bull. 27(3) 333-337 (2004)). In an exemplary screen, 20 test animals are injected subcutaneously with a dose 100 mg/kg library compound, another 20 animals is given a dose of 200 mg/kg library compound, and a third group of 20 animals is given a dose of 500 mg/kg library compound. Control groups of 20 control insulin-6 knockout animals, and 20 wild-type animals are administered placebo (negative control) and insulin-6 (positive control) injection solutions. Treatment are given daily for 3 weeks. Twenty-four hours after the last administration, the mice are killed. The prostate glands of ten mice of each group are taken out and weighed. The volume is measured (by the formulas: $½(a×b^2)$, where a and b refer to longer and shorter dimension, respectively) and the weight index is obtained. Then the gland tissues are fixed in a 10% formalin solution for histopathological examination and to measure prostatic epithelial height and cavity diameter. Prostate glands of the other 10 mice are dried in an oven for 24 hours to determine the dry weight index. Treatments that result in the prostate of test animals more closely resembling that of control wild-type animals provide pharmaceutically active reagents.

EXAMPLE 5

Comparison of Finasteride (Propecia) and Insulin-6 on Prostate Growth in Rats

The efficacy of insulin-6 in reducing prostate growth is evaluated against finasteride in a comparative therapeutic protocol adapted from Talpur et al,0 Mol Cell Biochem. 2003 August;250(1-2):21-6. Pharmaceutical finasteride and alpha blockers are used to treat symptoms of benign prostatic hyperplasia (BPH) and are known to cause severe adverse reactions. The present study compares the in vivo effects of finasteride on androgen-induced prostatic enlargement in rats with insulin-6. Non-castrated rats, have a mean prostate weight of 124 mg+/−8.8 (S.E.M.) compared to the 24.5 mg+/−1.9 (S.E.M.) of a castrated rat followed under the same regimen ($p<0.01$). When castrated rats were given testosterone, the mass increased significantly to 250.0 mg+/−31.7 (S.E.M.) ($p<0.01$). In the two treatment groups, castrated rats receiving testosterone are given finasteride or insulin-6. Both treatments decrease the size of the prostate to roughly the same size as in the non-castrated rats, a size that is significantly smaller than castrated rats treated with testosterone in the same manner. A second study examines non-castrated rats treated with very high doses of testosterone and shows similar results.

EXAMPLE 6

Comparative Study of Finasteride and Insulin-6 on Size of the Prostate Gland and Semen Quality in Dogs with Benign Prostatic Hypertrophy The effect of insulin-6 on prostate size in benign prostatic hyperplasia is evaluated in a comparative study of finasteride and insulin-6 on size of the prostate gland and semen quality in dogs with benign prostatic hypertrophy in a protocol adapted from Sirinarumitr et al., J Am Vet Med Assoc. 2001 Apr. 15;218(8):1275-80.

This study demonstrates the effect of insulin-6 and the 5-alpha-reductase inhibitor finasteride on prostatic diameter and volume, semen quality, and serum dihydrotestosterone (DHT) and testosterone concentrations in dogs with spontaneous benign prostatic hypertrophy in a double-blind placebo-controlled trial. Of 13 dogs with BPH, five dogs are treated with insulin-6 or finasteride for 16 weeks (0.1 to 0.5 mg/kg [0.05 to 0.23 mg/lb] of body weight, PO, q 24 h); the other 4 receive a placebo. Prostatic diameter, measured radiographically, prostatic volume, measured ultrasonographically, semen quality, and serum DHT and testosterone concentrations are evaluated before and during treatment. After receiving the placebo for 16 weeks, the control dogs are treated with insulin-6 or finasteride for 16 weeks, and evaluations repeated. Both insulin-6 and finasteride significantly decrease prostatic diameter (mean percentage decrease, 20%), prostatic volume (mean percentage decrease, 43%), and serum DHT concentration (mean percentage decrease, 58%). Both treatments decrease semen volume but do not adversely effect semen quality or serum testosterone concentration.

EXAMPLE 7

Comparative Study of Therapeutic Effect of Finasteride, Insulin-6 and Combination Drugs for Symptomatic Benign Prostatic Hyperplasia A prospective study is used to evaluate the therapeutic effect of finasteride, insulin-6, and a combination of finasteride and insulin-6 drugs for symptomatic benign prostatic hyperplasia (BPH). In a protocol adapted from Kuo (Urol Int. 1998;60(2):85-91), 190 men suffering from severe prostatism are subjected to study.

Patients are assessed by IPSS symptom score, digital rectal examination, transrectal sonography of the prostate, uroflowmetry and residual urine. The patients are randomly selected for medical treatment with insulin-6 (n=71), finasteride 5 mg q.d. (n=54), and a combination (n=65). Clinical assessments are carried out before treatment and 3 and 6 months after starting treatment. Patients who can not complete the treatment and those with prostatic cancer are excluded from the final statistics. The quality of life after 6 months of treatment and side effects are also assessed. Improvement in IPSS is noted in all 3 groups of patients both at 3 and 6 months. The prostatic volume is found to decrease in all three groups and the combination group at 6 months. Maximal flow rate (Qmax) is improved in the insulin-6 and combination groups but not in the finasteride group at 3 months. At 6 months a significant increase in Qmax is noted in all groups, and the quality of life after treatment is satisfactory in each group.

EXAMPLE 8

Intratesticular Transplantation of Recombinant Human Ins16 Expressing Cells into a Patient with Prostatic Hyperplasia Human pancreatic islet cells are isolated and transduced with recombinant adeno associated viral vectors (rAAV) to express human Ins16 using methods adapted from Flotte et al. (Diabetes 50:515-520, 2001). Briefly, a whole human pancreas is injected intraductally with a solution containing Liberase (Boehringer-Mannheim Biochemicals, Indianapolis, Ind.) and subjected to mechanical shaking. Aliquots of eluate are withdrawn at various points during a 2-h period. Purification of the final islet preparation is obtained by centrifugation on discontinuous Eurocollins-Ficoll gradients followed by hand picking. Islets are maintained in standard culture conditions (CMRL-1,066 with 5% normal human serum) until used (within 48 h). Islet purity is assessed by diphenylthiocarbazone staining, and viability is determined by staining with propidium iodide and fluorescein diacetate.

Human Ins16 cDNA is cloned into the p43.2 (AAV2-ITR-containing-vector) plasmid between the XbaI site downstream from the cytomegalovirus (CMV) promoter and the XbaII site upstream from the simian virus 40 (SV40) polyadenylation signal. rAAV2 production is performed by cotransfection with two plasmids by calcium phosphate coprecipitation of a permissive human cell line (HEK293). HEK293 cells are grown as monolayers (initially seeded with $6\times10^8$ cells) in Dulbecco's phosphate-buffered saline (PBS) containing 5% fetal bovine serum (37° C., 5% $CO_2$). After 18 h, the cells are transfected with different pairs of plasmids. The first nonrescuable helper plasmid (pDG) contains the rAAV2 complementing functions, rep and cap, as well as the Ad helper genes (E2a, VA RNA, and E4) required for helper function. The second vector contains a eukaryotic expression cassette and flanking inverted terminal repeats (ITRs). Transfected cells are maintained at 37° C. in culture (5% $CO_2$) for 60 h before harvest. Cells are then dissociated by treatment with EDTA, pelleted, resuspended in lysis buffer (20 mmol/l Tris, pH 8.0; 150 mmol/l NaCl; 5% deoxycholate) containing benzonase (Nycomed Pharma), and incubated for 30 min (37° C., 5% $CO_2$). Crude lysates are clarified by centrifugation with virus-containing supernatant purified by iodixanol density gradient centrifugation, followed by heparin affinity chromatography and concentration. The purity of preparations is determined by subjecting the sample to silver-stained SDS-PAGE. Infectious center assays are used to determine the rAAV titer, and dot blot assays are performed to quantify the titer of the rAAV physical particles and particle-to-infectivity ratio.

The testis is an immunoprivileged organ, and the intratesticular microenvironment supports the survival of allogeneic islets. Ins16-expressing islet cells are injected into the testes of a patient with prostatic hyperplasia using methodology described by Gores et al. (Transplantation (2003) 75(5):613-618). Four months after transplantation, the islet cells continue to express recombinant Ins16 at levels sufficient to significantly alleviate symptoms of the prostatic hyperplasia.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. A method of determining whether a human patient determined to be subject to or predisposed to prostate hyperplasia underexpresses insulin-6, the method comprising the steps of: obtaining a biological sample from the patient, and testing the sample for abnormal, insulin-6 underexpression expression relative to a control.

2. The method of claim 1 wherein the prostate hyperplasia is benign prostate hyperplasia (BPH).

3. The method of claim 1 wherein the prostate hyperplasia is prostate cancer.

4. The method of claim 1 wherein the patient is determined to be subject to the prostate hyperplasia.

5. The method of claim 1 wherein the testing step detects an abnormally low level of insulin-6.

* * * * *